United States Patent
Shinozuka et al.

(10) Patent No.: US 9,468,399 B2
(45) Date of Patent: Oct. 18, 2016

(54) DETECTION OF CHANGES FROM A SEATED OR LYING BODY POSITION BY SENSING BODY ANGLE

(71) Applicant: SensaRx, LLC, New York, NY (US)

(72) Inventors: Kenneth F. Shinozuka, New York, NY (US); Masato Mizuta, Minamishimabara (JP)

(73) Assignee: SensaRx, LLC, New York, NY (US)

( * ) Notice: Subject to any disclaimer, the term of this patent is extended or adjusted under 35 U.S.C. 154(b) by 43 days.

(21) Appl. No.: 14/565,169

(22) Filed: Dec. 9, 2014

(65) Prior Publication Data

US 2016/0157754 A1    Jun. 9, 2016

(51) Int. Cl.
| | |
|---|---|
| G08B 23/00 | (2006.01) |
| A61B 5/11 | (2006.01) |
| A44B 99/00 | (2010.01) |
| H05K 7/12 | (2006.01) |
| A61B 5/00 | (2006.01) |

(52) U.S. Cl.
CPC .............. *A61B 5/1115* (2013.01); *A44B 99/00* (2013.01); *A61B 5/6823* (2013.01); *A61B 5/6828* (2013.01); *H05K 7/12* (2013.01); *A44D 2200/10* (2013.01); *A61B 5/1116* (2013.01); *A61B 5/1126* (2013.01); *A61B 5/6804* (2013.01); *Y10T 24/3698* (2015.01)

(58) Field of Classification Search
CPC ............................ G08B 21/0446; A61B 5/68
USPC .......... 340/573.7, 573.1, 686.1, 671; 702/94, 702/153; 600/300; 604/19, 66
See application file for complete search history.

(56) References Cited

U.S. PATENT DOCUMENTS

| | | | |
|---|---|---|---|
| 806,521 | A | 12/1904 | Childs |
| 904,968 | A | 11/1908 | Kocher |
| 2,075,722 | A | 3/1937 | Illsche |
| 2,089,221 | A | 8/1937 | Patur |
| 2,121,147 | A | 6/1938 | Goodrich |
| 2,435,082 | A | 1/1948 | Huber |
| 3,376,991 | A | 4/1968 | Deaver |
| 3,392,729 | A | 7/1968 | Lenoir |
| 3,530,550 | A | 9/1970 | White |
| 3,790,014 | A | 2/1974 | Mucsi |
| 3,865,290 | A | 2/1975 | Sperling |
| 4,007,850 | A | 2/1977 | Beaugrand |
| 4,053,077 | A | 10/1977 | DeFelice |

(Continued)

FOREIGN PATENT DOCUMENTS

| | | |
|---|---|---|
| JP | 2-280733 A | 11/1990 |
| JP | 4-12733 A | 1/1992 |

(Continued)

OTHER PUBLICATIONS

Monbaby; You tube video; 2 pages; retrieved from the internet; (https:www.youtube.com/watch?v=s1y-LmvRrTk); Published Mar. 21, 2014 (Screenshot).

(Continued)

*Primary Examiner* — Toan N Pham
(74) *Attorney, Agent, or Firm* — Shay Glenn LLP (57) ABSTRACT

Methods and apparatuses for detecting when a subject gets up out of bed or out of chair by detecting changes in body flexion angle with respect to a threshold. Also described herein are systems for monitoring one or more subjects each wearing an angle-sensing unit.

17 Claims, 4 Drawing Sheets

(56) References Cited

U.S. PATENT DOCUMENTS

| | | |
|---|---|---|
| 4,084,716 A | 4/1978 | Bogert |
| 4,084,717 A | 4/1978 | King |
| 4,128,194 A | 12/1978 | Hinz |
| 4,175,305 A | 11/1979 | Gillis |
| 4,270,664 A | 6/1981 | Buono |
| 4,308,647 A | 1/1982 | Gillis |
| 4,461,394 A | 7/1984 | Sendel et al. |
| 4,519,175 A | 5/1985 | Resan |
| 4,617,771 A | 10/1986 | Tomaszewski |
| 4,658,558 A | 4/1987 | Verble |
| 4,702,443 A | 10/1987 | Callaway |
| 4,727,699 A | 3/1988 | Sargent |
| 4,934,547 A | 6/1990 | Mayes et al. |
| 4,972,980 A | 11/1990 | Parsons |
| 4,985,968 A | 1/1991 | Hooper |
| 4,999,963 A | 3/1991 | Verble |
| 5,067,642 A | 11/1991 | Fodge |
| 5,114,061 A | 5/1992 | Brady |
| 5,169,033 A | 12/1992 | Shay |
| 5,276,432 A | 1/1994 | Travis |
| 5,369,899 A | 12/1994 | Reeves |
| 5,511,289 A | 4/1996 | Melia |
| 5,522,849 A | 6/1996 | Xiques et al. |
| 5,557,830 A | 9/1996 | Davis |
| 5,610,877 A | 3/1997 | Adams et al. |
| 5,655,271 A | 8/1997 | Maxwell Trumble et al. |
| 5,676,270 A | 10/1997 | Roberts |
| 5,751,214 A * | 5/1998 | Cowley ............... A61B 5/0002 128/886 |
| 5,926,920 A | 7/1999 | Denison |
| 5,940,942 A | 8/1999 | Fong |
| 6,109,466 A | 8/2000 | Carrier |
| 6,199,247 B1 | 3/2001 | Tsai |
| 6,236,319 B1 * | 5/2001 | Pitzer ............... B63C 9/0005 340/572.8 |
| 6,239,706 B1 | 5/2001 | Yoshiike et al. |
| 6,295,703 B1 | 10/2001 | Adams et al. |
| 6,307,481 B1 | 10/2001 | Lehrman et al. |
| 6,501,386 B2 | 12/2002 | Lehrman et al. |
| 6,611,783 B2 | 8/2003 | Kelly et al. |
| 6,661,347 B2 | 12/2003 | Lehrman et al. |
| 6,703,939 B2 | 3/2004 | Lehrman et al. |
| 6,718,600 B1 | 4/2004 | Gillis |
| 6,913,157 B2 | 7/2005 | Oh |
| 7,071,820 B2 * | 7/2006 | Callaway ............... G08B 21/02 340/506 |
| 7,145,461 B2 | 12/2006 | Lehrman et al. |
| 7,216,404 B1 | 5/2007 | Doyle |
| 7,698,830 B2 * | 4/2010 | Townsend ............. A61B 5/1116 33/341 |
| 7,784,158 B2 | 8/2010 | Doyle |
| 8,317,067 B2 | 11/2012 | Lewis |
| 8,327,510 B2 | 12/2012 | Schlesinger |
| 8,428,696 B2 * | 4/2013 | Foo ............................ 600/509 |
| 8,453,866 B2 | 6/2013 | Kamath |
| 8,590,719 B2 | 11/2013 | Sprishen et al. |
| 8,695,170 B2 | 4/2014 | Honeycutt |
| 8,736,439 B1 | 5/2014 | Shinozuka |
| 8,814,811 B2 | 8/2014 | Scholten et al. |
| 8,866,620 B2 * | 10/2014 | Amir ............... G08B 21/043 340/573.1 |
| 2003/0014844 A1 | 1/2003 | Splane |
| 2008/0023508 A1 | 1/2008 | Harchol |
| 2013/0085418 A1 * | 4/2013 | Salhani ............... A61B 5/0002 600/595 |
| 2014/0313030 A1 * | 10/2014 | Ten Kate ............. A61B 5/1115 340/539.12 |

FOREIGN PATENT DOCUMENTS

| | | |
|---|---|---|
| JP | 11-177662 A | 7/1999 |
| JP | 3093745 B2 | 7/2000 |
| JP | 3322632 B2 | 6/2002 |
| JP | 200361935 A | 3/2003 |
| JP | 200595228 A | 4/2005 |
| WO | WO2010/099294 A1 | 9/2010 |
| WO | WO2014/029594 A2 | 2/2014 |

OTHER PUBLICATIONS

Monbaby; The only baby monitor in a smart button; product brochure; 5 pages; © 2014; retrieved Jun. 10, 2015 from the internet; (https:monbaby.com).

Weissman; Indoor Location (white paper); 16 pages; © 2004; retrieved Jun. 23, 2015 from the internet; (http://www.tadlys.co.il/media/downloads/Indoor_location_Systems.pdf).

Shinozuka et al.; U.S. Appl. No. 14/702,398 entitled "Affixation of objects to garments," filed May 1, 2015.

Shinozuka et al.; U.S. Appl. No. 14/703,792 entitled "Devices and methods for indoor geolocation," filed May 4, 2015.

* cited by examiner

DETECTION OF CHANGES FROM A SEATED OR LYING BODY POSITION BY SENSING BODY ANGLE

CROSS REFERENCE TO RELATED APPLICATIONS

None.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Methods and apparatuses (including devices and systems) for detecting when a subject gets up out of a bed or chair. In particular, described herein are methods and apparatuses for determining a change in body angle (body flexion angle) relative to an initial position to alert a caregiver that a subject being monitored has gotten up from a bed or chair.

BACKGROUND

There are an increasing number of people globally for whom transitions from a bed or chair subject them to a risk of accidental harm. For example, the elderly, those suffering from debilitating diseases, and those suffering from dementia (including Alzheimer's dementia) as well as other mental and medical conditions are at risk when transitioning from a sitting or lying position. For example, for the elderly and/or infirm, accidents and injuries may occur as a result of wandering out of a bed or chair. However, the need for constant vigilance may cause significant stress to caregivers in home, hospitals and nursing facilities. It would be beneficial to provide methods and systems for detection and alerting of bed and/or chair leaving events, which could not only enhance the safety of subjects but also alleviate the stress of their caregivers. Further, it would also be beneficial to provide one or more methods and apparatuses for detecting and alerting caregivers of such transitions to prevent illness/accidents by remotely monitoring subject's routine activities without requiring the use of cameras due to privacy concerns.

Previous systems for monitoring subjects to prevent falls or wandering typically require more complex, and therefore expensive, methods to track subject movement. For example, Japanese Laid-Open Patent Application No. 2-280733 describes the use of load sensors installed on a subject's bed to detect his or her bed departure, and uses weight information to determine whether a user is still on the bed or has left the bed. Similarly, Japanese Patent No. 3093745, Japanese Patent No. 3322632, and U.S. Pat. No. 5,276,432 each describe the calculation of a subject's center of gravity from weight information of four points on a bed and use the center-of-gravity position information to monitor the movement of a user in bed. U.S. Pat. No. 6,239,706 disclosed describes an in-bed state determination based on measured load characteristics. These references, and similar techniques, all require specialized beds installed with load sensors (or retrofitted beds). The associated costs and cumbersome set-up prevent their wide applications in homes as well as in nursing facilities and hospitals.

As another solution, U.S. Pat. No. 8,736,439 uses a sensor sock to detect an individual leaving the bed by detecting a change in foot pressure. However, not all patients are comfortable wearing socks (especially when sleeping).

Alternatively, U.S. Pat. No. 6,307,481, U.S. Pat. No. 6,501,386, U.S. Pat. No. 6,661,347, U.S. Pat. No. 6,703,939, U.S. Pat. No. 6,864,796, U.S. Pat. No. 7,095,331, U.S. Pat. No. 7,145,461, and U.S. Pat. No. 7,479,890 describe systems to evaluate movement of a body relative to an environment by sensing dynamic and static accelerative phenomena, and determines whether the evaluated body movement is within an environmental tolerance. Unfortunately assumptions typically made by such systems about the patient's environment may not be accurate, or may lead to artifacts. In addition, such systems may be expensive and difficult to operate.

Finally, U.S. Pat. No. 8,814,811 describes a fall detection algorithm based on both the dynamic acceleration and static position signals and the high sampling rate required for acquiring the dynamic signal consumes energy.

Described herein are methods and apparatuses that may address the issues discussed above. For example, described herein are methods and apparatuses that may detect and notify caregivers that a patient being monitored (a subject) has changed body position in a manner that corresponds specifically with getting out of a bed or getting out of a chair. These apparatuses and methods are simple, relatively low-cost and easy to implement.

SUMMARY OF THE DISCLOSURE

Described herein are simple and reliable methods and a low-cost apparatuses (including device and systems) to sense when a subject has gotten out of a bed or chair, and to remotely inform or alert caregivers. This may address the needs for not only detecting and alerting patients' wandering out of bed/chair, but also remotely monitoring a subject's routine life to detect illness and other unusual events. A subject, as used herein, may include a patient, or any other person in need of the monitoring described herein; subjects are not limited to hospital/medical patients, although the term "subject" and "patient" may be used interchangeably herein.

In general, a subject to be monitored wears a small angle-sensing unit, which can be directly adhered to the subject's body, or affixed on the clothes, pajama, briefs, a belt or an accessory worn by the subject. The angle-sensing unit may preferably be tightly attached to the subject's body to accurately measure the subject's body angle. The unit may be oriented (e.g., so that an axis of the angle-sensing unit is generally oriented along the longitudinal axis of the subject) when placed on the subject. The unit generally includes an angle sensor that may measure an inclination angle (e.g. a static angle relative to gravity, for example), a microcontroller, a wireless transmitter, and a power supply. When the subject lies down on a bed or sits down on a chair, his or her initial body position may be set as a baseline. This may be done manually, e.g. by the monitoring caregiver, or automatically. When the subject changes his or her body angle by getting up, the sensor may detect a new body angle; if this new body angle exceeds the baseline angle by a predetermined amount (e.g., equivalent to greater than +/−20°, 25°, 30°, 35°, 40°, 45°, 50°, 55°, 60°), the microcontroller may transmit a wireless signal, directly or through a server, to the caregiver's monitoring unit ("monitoring receiver"), which can be a smartphone, a smart watch, a tablet, a PC, a nurse station monitor, or a custom-made monitor. Various alerts can be issued on the monitor depending on whether the intended purpose is to detect wandering of a patient or an unusual event in daily routine life.

A plurality of the angle-sensing units can be monitored simultaneously by a single monitoring unit. Furthermore, the angle-sensing units and the monitoring unit can be further linked to a server through the internet to form a service system.

These methods and system have numerous advantages over existing systems. For example, the body angle sensors described herein may detect a subject's getting up from the bed or the chair before his or her foot lands on the floor, which can prevent fall accidents. Further, by comparing the body angle (e.g., static body angle) with respect to its own baseline, the detection of the change in body becomes reliable.

In addition, the angle sensor may be positioned to measure gross body flexion angle only, and any rotations of the body in other directions will not affect the reliability of the detection.

Furthermore, to measure the static angle (rather than the dynamic acceleration), a low sampling rate (such as once every second) may be sufficient to sample the angle sensor, which may significantly save the power consumption, and reduce or eliminate the need for bulky batteries and may make the sensor circuit more wearable. Finally, the apparatuses described herein are easy to set up and operate, and may be produced and operated for very low cost.

Thus, described herein are methods of issuing an alert when a subject wearing an angle-sensing unit gets up from a bed or a chair. For example, such a method may comprise: setting, in a microcontroller connected to an angle sensor in the angle-sensing unit, a first value representing a first angle of the angle-sensing unit when the subject is sitting in a chair or reclined in a bed; sampling the angle sensor to determine a sampled value representing a sampled angle of the sensor; determining a difference between the sampled value and the first value to detect a change in the subject's body angle; and wirelessly transmitting an alert if the difference between the sampled value and the first value exceeds a threshold indicating that the subject has gotten up from the bed or out of the chair.

As mentioned, in general, setting the first value may comprise manually setting the first value once the subject reclines on a bed or sits in a chair. This may be performed by the caregiver, e.g., at the angle-sensing unit (by pressing a control, e.g., button, knob, dial, etc.) and/or at the monitoring station in communication with the sensor. Alternatively, the first value may be set automatically, shortly after being applied to the subject, by sampling the angle-sensing unit once it has been attached to the subject, assuming that the subject is in the initial position (e.g., recumbent on a bed, sitting in a chair, etc.).

The angle sensor of the angle-sensing unit may be sampled at any sampling rate, such as once every second (e.g. 1 Hz), or once every two seconds (0.5 Hz). The sample rate may be modified or set by the caregiver. Sampling may comprise sampling the angle sensor at a preferred sampling rate to determine the sampled value.

In some variations the microcontroller compares the first (e.g., baseline) angle value to sensed angle values, or more accurately for both baseline and sensed angle values, values representing the angle of the angle-sensing unit and therefore body angle, in the angle-sensing unit; in some variations the angle-sensing unit transmits the sensed angle to a processor that is remote to the angle-sensing unit for performing the calculations.

In determining if an alert should be transmitted (or in some variations as mentioned above, simply raised) the apparatus may filter (e.g., average, limit, etc.) or select samples from the angle sensor that will be compared with the baseline value. In variations in which the angle sensor is detecting static angle of the angle-sensing unit (and therefore the subject's body) relative to gravity, for example, the value compared to the baseline (as well as the initial selection of the baseline) may be determined as a 'stable' or settled value, averaged (e.g., window averaged) or filtered to reduce other motion (and in particular other acceleration) artifacts. For example, either or both the steps of setting the first value and sampling the angle sensor may comprise measuring a static angle of the angle-sensing unit attached to the subject; in some variations the angle sensor comprises a single-axis accelerometer, or a 3-axis accelerometer.

In general, the methods described herein may include receiving the alert (e.g., at a monitoring unit) indicating that the subject wearing the angle-sensing unit has gotten up from a bed or out of a chair. Wirelessly transmitting an alert may include transmitting a signal to a monitoring receiver. The signal may be converted to one or more of: an audible sound, illuminating light, vibrating notification, or text message at the monitoring unit. Wirelessly transmitting an alert may include transmitting a wireless signal to a server through a monitoring unit or a gateway, wherein the server records the wireless signal into a database and provides data service to subscribing users.

Any of the methods described herein may also include attaching the angle-sensing unit to the subject, and/or instructing a caregiver to attach the angle-sensing unit to the subject. Attaching may be made in a specific manner, so that the angle-sensing unit (and in particular the angle sensor in the angle-sensing unit) is oriented relative to the subject's body. For example, it may be advantageous to attach the angle-sensing unit along the long axis of the subject's body (e.g., torso, neck, head, waist, thighs, etc.) with the angle-sensing unit configured so that an indicator (e.g., arrow, line, point, alphanumeric text, etc.) is oriented in the long axis, such as up towards the subject's head/crown or down toward their feet. In general, it may be beneficial to orient the axis of the angle-sensing unit (and particularly the angle sensor) approximately along the long axis of the subject (e.g., within +/−5°, 10°, 15°, 20°, etc.). Thus, any of the apparatuses described herein may include an indicator on the angle-sensing unit indicating the proper orientation of the angle-sensing unit relative to the subject's head, feet, etc. In some variations the system, such as the monitoring unit, may check with the caregiver to confirm that the angle-sensing unit is being worn by the subject with the angle-sensing unit oriented in the subject's long axis.

As mentioned, the angle-sensing unit may be worn directly on the subject's body (e.g., on their skin, adhesively attached, worn on a band or strap, etc., or it may be worn on (and/or integrated into) a garment worn by the subject, including (but not limited to) clothes, pajamas, hospital gown, briefs, a belt, or an accessary worn by the subject, or a medical device (e.g., catheter, tube, etc.). The angle-sensing unit may be worn tightly on the subject's body for accurate measurement of the subject's body angle.

Also described herein are methods of monitoring a plurality of subjects each wearing an angle-sensing unit and issuing an alert when one of the plurality of subject gets up from a bed or a chair. For example, a method may include: setting, for each angle-sensing unit worn by one of the subjects in the plurality of subjects, a first value representing a first angle for the angle-sensing unit when the subject wearing the sensor is sitting in a chair or reclined in a bed; sampling, for each angle-sensing unit worn by one of the subjects in the plurality of subjects, an angle sensor of the angle-sensing unit to determine a sampled value representing a sampled angle of the sensor; determining, for each angle-sensing unit worn by one of the subjects in the plurality of subjects, a difference between the sampled value and the first value to detect a change in a body angle for the subject wearing each angle-sensing unit; and wirelessly transmitting, for each angle-sensing unit worn by one of the subjects in the plurality of subject's, an alert if the difference between the sampled value and the first value exceeds a threshold indicating that the subject has gotten up from the bed or out of the chair, wherein the alert comprises an identification number or name uniquely associated with the transmitting angle-sensing unit.

As described above, setting may comprise manually setting, for each angle-sensing unit worn by one of the subjects in the plurality of subjects, the first value once the subject reclines on a bed or sits in a chair. One or more alerts may be received (e.g., at a monitoring unit) indicating that one of the subjects has gotten up from a bed or out of a chair and identifying the angle-sensing unit transmitting the alert.

Thus, in any of the method and apparatuses described herein, an angle-sensing unit may include a unique (or may be caregiver-marked with a unique) identifier that corresponds to the subject wearing the angle-sensing unit. The unique identifier may be an alphanumeric, numeric, or the like, and may be transmitted with any of the transmissions (including but not limited to alerts) from the angle-sensing unit.

In some variations the monitoring unit may be configured to trigger an alert if the apparatus does not check in within a predetermined time period. For example, in some variations the system (e.g., the monitoring unit) may trigger an alert when periodic signals (including signals indicating that the body angle is not above the threshold indicating that the subject has gotten up) are not received as expected. For example, in some variations, the method may include generating an alert at a remote monitoring unit if a wireless transmission is not received for each angle-sensing unit worn by one of the subjects in the plurality of subject's within a predetermined amount of time.

Also described herein are angle-sensing unit apparatus configured to determining when a subject wearing the apparatus gets up from a bed or a chair. For example, an angle-sensing unit apparatus may include: a wireless transmitter; an angle sensor configured to produce a signal corresponding to a static angle of the angle-sensing unit relative to a direction of gravity; a microcontroller connected to the wireless transmitter and to the angle sensor, the microcontroller configured to store a first value from the angle sensor representing a first angle of the angle-sensing unit when a subject wearing the angle-sensing unit is sitting in a chair or reclined in a bed, further wherein the microcontroller is configured to sample the angle sensor at a pre-determined sampling rate and determine a difference between the sampled values and the first value to detect a change in the subject's body angle and to wirelessly transmitting an alert if the difference between the sampled values and the first value exceeds a threshold indicating that the subject has gotten up from the bed or out of the chair. As mentioned above, the angle sensor may be, e.g., a single-axis or a 3-axis accelerometer. Any of the apparatuses described herein may be configured (and may include any appropriate structure) to perform the functions described above. For example, any of the apparatuses described herein may be configured so that they include an orientation marking and/or structure indicating the alignment to be worn by the subject, and specifically, indicating that the device should be worn oriented in the subject's long axis of the subject's body (e.g., pointing towards the head, etc.).

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

In general, described herein are methods and apparatuses (e.g., devices such as angle-sensing units and systems including one or more angle-sensing units and/or one or more monitoring unit) that can determine a change in gross body angle indicating that a subject wearing the device has gotten up and/or out of a bed, and in some variations a chair.

Figure 1:
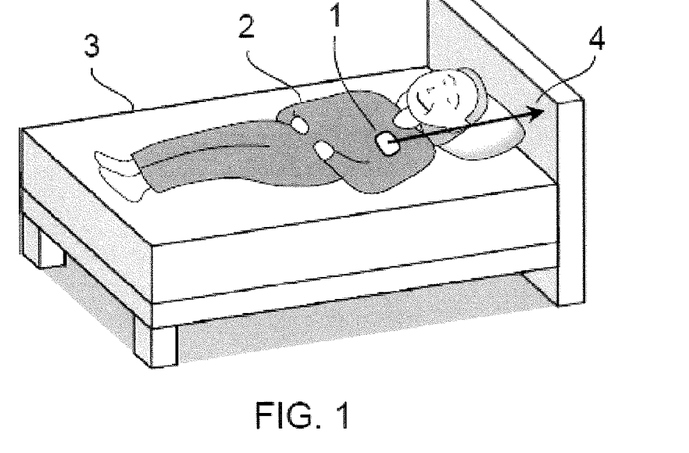
FIGS. 1 and 2 illustrate one example of a method and apparatus for detecting a subject's getting up from bed.

For example, FIG. 1, schematically illustrates operation of one variation of an angle-sensing unit. In FIG. 1, a subject 2 is shown lying down on a bed 3 wearing an angle-sensing unit 1 on his or her body. In general, the angle-sensing unit can be directly adhered to the subject's body, or affixed on the clothes, pajama, briefs, a belt or an accessory worn by the subject. The unit may be tightly attached to the subject's body to accurately measure the subject's body angle. The unit is oriented so that the initial body position 4 is detected (e.g., measured) by the sensor unit 1. This value may be set (e.g., automatically or manually by a caregiver) as the baseline body angle (e.g., a first angle of the angle-sensing unit). The angle-sensing unit may be oriented so when it is worn an axis of an angle sensor within the angle-sensing unit is approximately aligned with the long axis of the subject's body.

Figure 2:
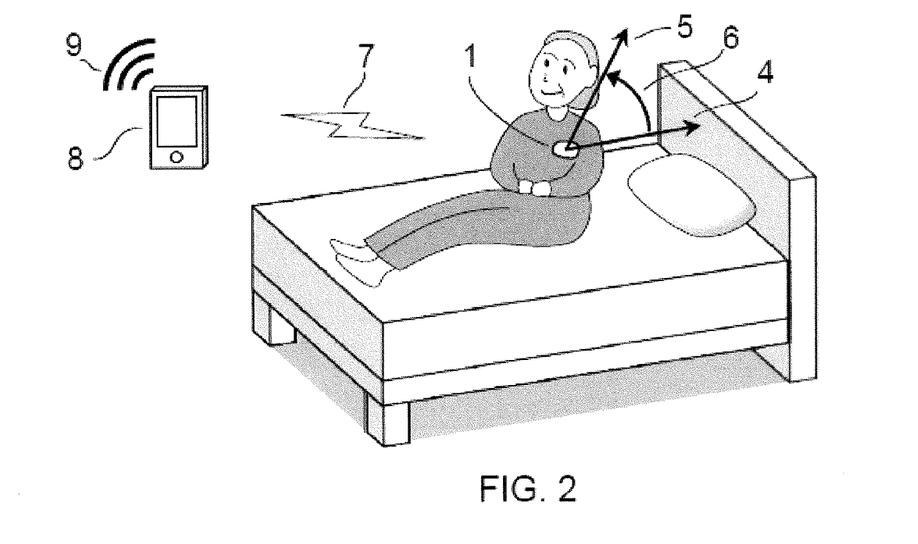

As shown in FIG. 2, when the subject 2 sits up, the body position and angle (as reflected by the angle of the angle-sensing unit) changed to a new position 5, and the body flexion angle 6 between the new position 5 and the baseline position 4 may be measured by the sensor 1. As will be described in greater detail below, an angle sensor within the angle-sensing unit may detect the static angle of the angle-sensing unit relative to gravity ("down") in the initial baseline position, and the angle-sensing unit may compare a value (e.g., a component of the acceleration due to gravity in a single axis, that may be approximately aligned with the subject's long axis) to the new value(s) sensed by the angle-sensing unit, as shown in FIG. 2. In this example, note that the angle-sensing unit does not need to calculate a complete angle, but may instead operate on the sensed values (current/voltage output by the accelerometer) representing these angles, and which may be converted to actual angle measurements. Thus, for example, the threshold values referred to herein may be in the same units as the sensed values for direct comparison (e.g., as acceleration values), but may correspond to threshold angles as recited herein.

In the example shown in FIGS. 1 and 2, when the measured angle 6 exceeds a pre-determined threshold, the angle-sensing unit 1 may wirelessly sends a signal 7 to a monitoring unit 8, which can be a caregiver's unit. When the monitoring unit receives the signal 7, the monitoring unit 8 may generate an alert (e.g., an audible sound 9, and/or text alert, and/or vibration alert, and/or visual alert). The alert may also (or alternatively) include a light illumination. The monitoring unit 8 can be a smartphone, a smart watch, a tablet, a PC, or a custom-made monitor. The wireless signal 7 can be transmitted through Bluetooth, Wi-Fi, ZigBee, Ant, or any wireless technologies.

Figure 3:
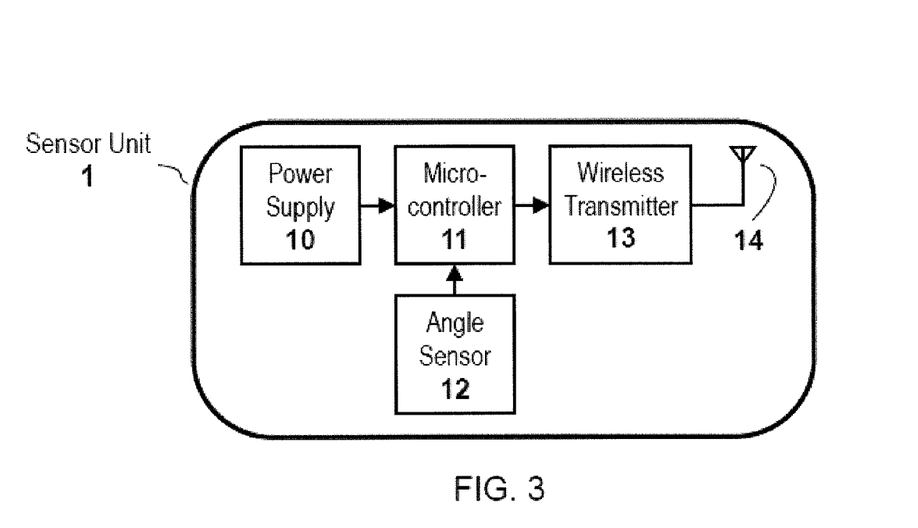
FIG. 3 is a schematic illustration of one embodiment of a sensor unit for detecting body angle, and therefore a change from sitting or lying positions. This sensor may include an angle sensor, a microcontroller, a wireless transmitter, and a power supply.

FIG. 3 shows one example of a detailed schematic view of a preferred embodiment of an angle-sensing unit 1, comprising a power supply 10, the microcontroller 11, angle sensor 12, wireless transmitter 13, and a wireless antenna 14. The angle sensor 12 may generally measure the body angle 6, and the microcontroller 11 acquires the sensor data and compare the sensor data with the pre-determined body angle threshold (e.g., equivalent to greater than about +/−20°, 25°, 30°, 35°, 40°, 45°, 50°, 55°, 60°). When the angle 6 exceeds the threshold, the microcontroller 11 may determine that the subject has gotten up from the bed, and subsequently commands the transmitter 13 to send a wireless signal 7 through antenna 14.

Figure 4:
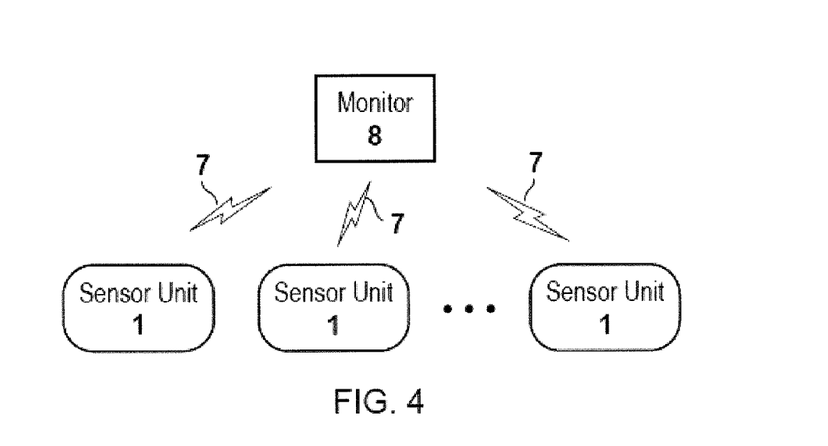
FIG. 4 is a schematic view showing a monitoring unit monitoring a plurality of sensor units.

FIG. 4 is a schematic view of an embodiment of the sensor system, comprising a single monitoring unit 8 and a plurality of sensor units 1, each worn by a subject and uniquely identified by a number or name. This system allows one caregiver to monitor multiple subjects. When any of the sensor units sends a wireless signal to the monitoring unit, the monitor will issue an alert showing the specific identification number of the subject's name.

Figure 5:
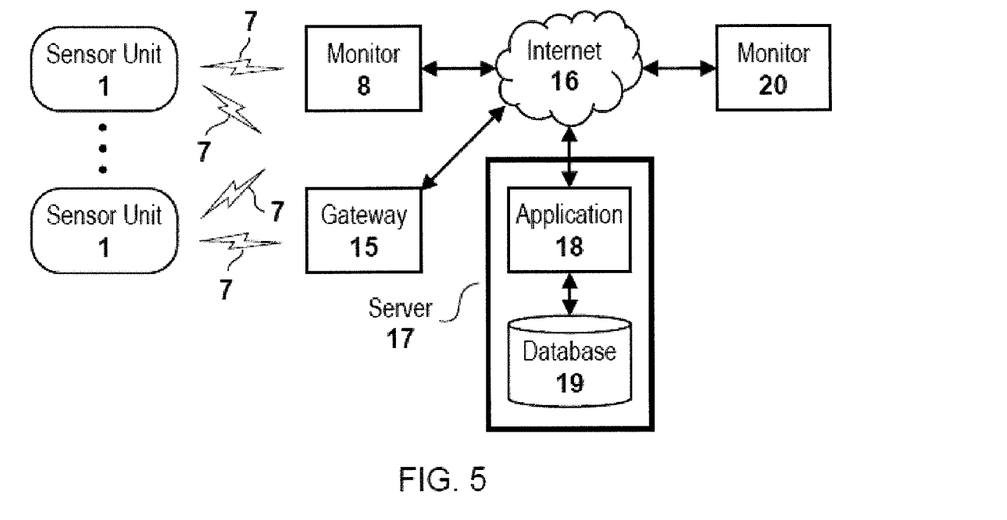
FIG. 5 is a schematic view of a system for detecting body angle and notifying one or more caregivers that a subject (or subjects) has changed from sitting or lying positions. The system may include sensor units, a monitor, a gateway, and a server.

Sensor units 1 can be further linked to a server to form a service system that records and reports the subjects' history of data monitored by the sensor units 1. FIG. 5 is a schematic view of an embodiment of a service system comprising the angle-sensing unit(s) 1, a monitoring unit 8, a gateway unit 15, Internet 16, a server 17, an application 18, a database 19, and an additional monitoring unit 20. The angle-sensing unit(s) 1 may be connected to an internet 16 and further to the server 17 via the monitoring unit 8 or the gateway unit 15. Data from sensor unit 1 may be stored in the database 19. The application 18 associated with the database 19 may run on the server 17. The additional monitoring unit 20 allows additional users(s) to receive the alert 7 and subscribe to data service.

The benefit of having the gateway unit 15 such as that shown in FIG. 5 is that the monitoring unit 8 can be placed at a remote location beyond the wirelessly communicable range to the sensor unit 1, as long as the gateway is within the wirelessly communicable range to the sensor unit 1.

Figure 6:
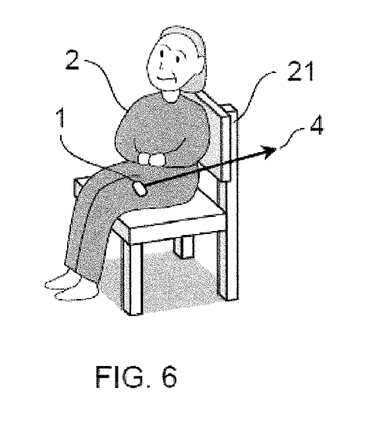
FIGS. 6 and 7 illustrate a method and apparatus for detecting a subject's getting up from a chair, as described herein.
Figure 7:
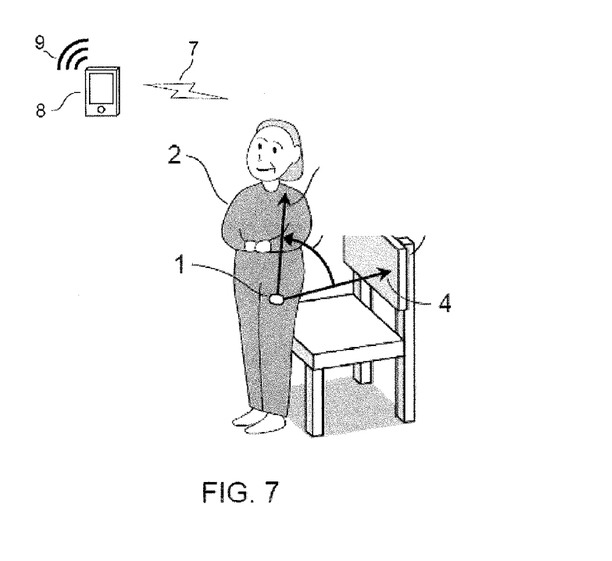

The methods and apparatuses described herein may also be used to detect when a subject rises out of a chair, as illustrated in FIGS. 6 and 7. In this example, the apparatus is shown detecting a subject getting up from a chair. In FIG. 6, the subject 2 wearing the angle-sensing unit is shown sitting on a chair 21, wearing the angle-sensing unit 1 on his or her thigh. In general, the angle-sensing unit can be directly adhered to the subject's body, or affixed on the clothes, pajama, briefs, a belt or an accessory worn by the subject. The unit may preferably be tightly attached to the subject's body. The initial thigh position (angle) 4 measured by the sensor unit 1 may be set as the baseline thigh angle as discussed above. For example, this may be the angle or equivalent value relative to gravity ("down") using a single-axis or a 3-axis accelerometer. As the subject 2 gets up, the thigh position changes to a new position 5, having a new body angle. This change in body angle may be detected by the apparatus as the angle 6 between the new position 5 and the baseline position 4, e.g. as measured by the angle sensor of the angle-sensing unit 1. When this difference in the measured angle from the baseline 6 exceeds a pre-determined threshold (e.g., equivalent to greater than +/−20°, 25°, 30°, 35°, 40°, 45°, 50°, 55°, 60°, or between any of these angles (e.g., between about 20° and 60°, etc.), the sensor unit 1 wirelessly sends a signal 7 to the monitoring unit 8, which can be a caregiver's unit. When it receives the signal 7, the monitoring unit 8 generates an alert, such as an audible sound 9 and/or a vibrating notification and/or a light illumination, etc. The monitoring unit 8 can be a smartphone, a smart watch, a tablet, a PC, or a custom-made monitor. The wireless signal 7 can be transmitted through Bluetooth, Wi-Fi, ZigBee, Ant, or any wireless technologies.

Although the example shown in FIGS. 6 and 7 include the sensor positioned on the subject's thigh, in practice the sensor may be positioned at other locations, including on the subject's torso, and may detect, for example, the subject leaning forward when standing to get out of the chair; although a transient motion, if the sample rate for the sensor is sufficiently high (e.g., greater than a few times per second) the change in position, including the change in static angle, may be accurately sensed. However, in general, there may be preferred locations for placement of the angle-sensing units described herein, including on the subject's thigh, particularly for use in detecting standing from a sitting position, and on the subjects torso, neck or head, which may be particularly sensitive for detecting sitting up to get out of bed.

Figure 8A:
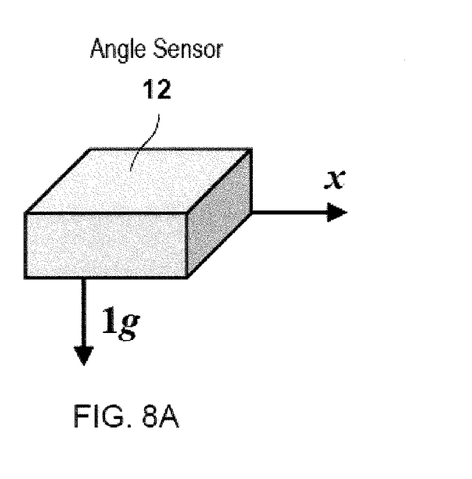
FIGS. 8A-8B illustrate one example of a sensor (e.g., shown in this example as a single-axis accelerometer) that may be used to detect a change in body angle as described herein.
Figure 8B:
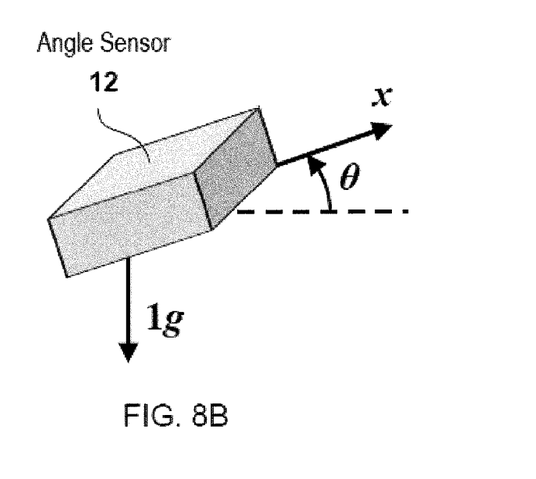

As mentioned above, in any of these variations, the angle-sensing unit includes an angle sensor. FIGS. 8A and 8B schematically illustrate a single-axis accelerometer that may be used as an angle sensor as described herein. Other angle sensors may be used (including multi-axis accelerometers including 3-axis accelerometers, gravity sensors, etc.). In reference to FIGS. 8A and 8B, as an example, a single-axis accelerometer can be used to measure the static angle of the human body. When the accelerometer axis X is tilted with an angle θ with respect to the horizontal plane (e.g., perpendicular to the direction of gravity, g), the accelerometer measures the vector component of the gravitational acceleration g projected to the X-axis, i.e.:

$$A_x = g \times \sin(\theta)$$

where $A_x$ is the accelerometer's output acceleration. Therefore, the angle can be calculated as:

$$\theta = \sin^{-1}\left(\frac{A_x}{g}\right).$$

In this example, the output value of the single-axis accelerometer may be particularly useful to approximate body angle, particularly when the x axis (which may be referred to as the axis of the angle sensor or the axis of the angle-sensing unit) is aligned with the long axis of the subject's body, generally extending from the top of the head to the feet. Further, it may be beneficial to measure only the static angle, separating out or ignoring the (rapidly-changing) dynamic forces on the sensor due to the movement (e.g., when sitting up). This may be achieved by filtering, averaging, and/or windowing the detected values. For example, rapid changes in the output of the angle sensor of the angle-sensing unit (e.g., the single-axis accelerometer) may be ignored in favor of static (steady-state) values, which may be persistent for two or more (e.g., 3, 4, 5, 6, 7, 8, etc.) sequential samples. The microcontroller may analyze the output of the angle sensor to make these determinations.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of issuing an alert when a subject wearing an angle-sensing unit gets up from a bed or a chair, the method comprising:

manually setting, in a microcontroller connected to an angle sensor in the angle-sensing unit, a first baseline value representing an initial angle measured by the angle sensor when the subject is sitting in a chair or reclined in a bed, wherein a caregiver manually sets the baseline value;

sampling the angle sensor to determine a sampled value representing a sampled angle of the subject's body angle;

determining a difference between the sampled value and the first baseline value to detect a change in the subject's body angle;

wirelessly transmitting an alert if the difference between the sampled value and the first baseline value exceeds a threshold indicating that the subject has gotten up from the bed or out of the chair; and receiving the alert at a monitoring unit wirelessly.

2. The method of claim 1, further wherein receiving the alert at the monitoring unit comprises receiving the alert in one of: a smartphone, a smart watch, a tablet, a PC, or a dedicated monitor.

3. The method of claim 1, wherein setting the first baseline value comprises measuring a static angle by the angle sensor in the angle-sensing unit attached to the subject.

4. The method of claim 1, further comprising attaching the angle-sensing unit to the subject.

5. The method of claim 1, wherein sampling the angle sensor to determine a sampled value comprises averaging a plurality of samples to determine the sampled value.

6. The method of claim 1, wherein wirelessly transmitting the alert comprises transmitting a signal to a monitoring unit, further wherein the signal is converted to one or more of an audible sound, illuminating light, vibrating notification, or text message at the monitoring unit.

7. The method of claim 1, wherein wirelessly transmitting comprises transmitting a wireless signal from the angle sensing unit to a server through a monitoring unit or a gateway, wherein the server wirelessly transmits the alert.

8. The method of claim 7, wherein wherein the server records the wireless signal into a database and provides data service to subscribing users.

9. The method of claim 1, further compromising attaching the angle-sensing unit on the subject's waist, chest, or thigh.

10. The method of claim 1, further compromising attaching the angle-sensing unit on the subject's clothes, pajamas, briefs, a belt, or an accessory worn by the subject.

11. A method of monitoring a plurality of subjects each wearing an angle-sensing unit and issuing an alert when one of the plurality of subject gets up from a bed or a chair, the method comprising:

manually setting, for each angle-sensing unit worn by one of the subjects in the plurality of subjects, a first baseline value representing an initial angle measured by an angle sensor in the angle-sensing unit when the subject wearing the sensor is sitting in the chair or reclined in the bed, wherein a caregiver manually sets the baseline value;

sampling, for each angle-sensing unit worn by one of the subjects in the plurality of subjects, the angle sensor to determine a sampled value representing a sampled angle of the subject's body angle;

determining, for each angle-sensing unit worn by one of the subjects in the plurality of subjects, a difference between the sampled value and the first baseline value to detect a change in a body angle for the subject wearing each angle-sensing unit;

wirelessly transmitting, for each angle-sensing unit worn by one of the subjects in the plurality of subject's, an alert if the difference between the sampled value and the first baseline value exceeds a threshold indicating that the subject has gotten up from the bed or out of the chair, wherein the alert comprises an identification number or name uniquely associated with the transmitting angle-sensing unit; and receiving the alert at a monitoring unit wirelessly, wherein the alert indicates that one of the subjects has gotten up from a bed or out of a chair, and identifying the angle-sensing unit transmitting the alert.

12. The method of claim 11, wherein receiving the alert at the monitoring unit comprises receiving the alert on a: a smartphone, a smart watch, a tablet, a PC, a nurse station monitor, or a dedicated monitor.

13. The method of claim 11, wherein setting comprises, for each angle-sensing unit worn by one of the subjects in the plurality of subjects, measuring a static angle by the angle sensor in the angle-sensing unit attached to the subject.

14. The method of claim 11, wherein wirelessly transmitting comprises transmitting a wireless signal from the angle sensing unit to a server through a monitoring unit or a gateway, wherein the server wirelessly transmits the alert.

15. The method of claim 14, wherein wherein the server records the wireless signal into a database and provides data service to subscribing users.

16. An angle-sensing unit apparatus configured to determining when a subject wearing the apparatus gets up from a bed or a chair, the apparatus comprising:

a wireless transmitter;

angle sensor configured to produce a signal corresponding to a static angle of the angle-sensing unit relative to a direction of gravity;

a microcontroller connected to the wireless transmitter and to the angle sensor, the microcontroller configured to store a first baseline value from the angle sensor representing an initial angle of the angle-sensing unit when a subject wearing the angle-sensing unit is sitting in the chair or reclined in the bed wherein the microcontroller is configured to store the first baseline value when a caregiver manually activates a control;

further wherein the microcontroller is configured to sample the angle sensor and determine a difference between the sampled values and the first value to detect a change in the subject's body angle and to wirelessly transmitting an alert if the difference between the sampled values and the first value exceeds a threshold indicating that the subject has gotten up from the bed or out of the chair.

17. The apparatus of claim 16, wherein the angle sensor comprises an accelerometer.

* * * * *